United States Patent [19]
Butler

[11] Patent Number: 5,164,165
[45] Date of Patent: Nov. 17, 1992

[54] DRINKING FOUNTAIN APPARATUS

[76] Inventor: Alfred E. Butler, 405 Hickory La., Burnsville, N.C. 98714

[21] Appl. No.: 719,617

[22] Filed: Jun. 24, 1991

[51] Int. Cl.$^5$ ............................................. A61L 2/00
[52] U.S. Cl. ............................... 422/292; 422/28; 222/185
[58] Field of Search ............ 422/292, 28, 295; 222/148, 185, 529, 537; 239/302, 379

[56] References Cited

U.S. PATENT DOCUMENTS

| | | | |
|---|---|---|---|
| 395,652 | 1/1889 | Burton | 222/185 |
| 636,375 | 11/1899 | Beariks | 222/175 |
| 2,020,711 | 5/1934 | Warr | 222/529 |
| 2,056,863 | 10/1936 | Napier | 222/185 |
| 3,107,975 | 10/1963 | Linder | 422/295 |
| 3,203,631 | 8/1965 | Jutila | 239/379 |
| 3,966,093 | 6/1976 | Frahm et al. | 222/185 |
| 4,386,718 | 6/1983 | Stewart et al. | 222/185 |

FOREIGN PATENT DOCUMENTS 212578  2/1955  Australia .............................. 222/175

Primary Examiner—Robert J. Warden
Assistant Examiner—Laura E. Collins
Attorney, Agent, or Firm—Leon Gilden

[57] ABSTRACT

A drinking fountain includes a fluid reservoir with an outlet conduit and valve mounted to the reservoir adjacent a lower terminal end thereof. The outlet conduit receives a fluid directing conduit defined by a first central tube leg and a second tube leg mounted at an oblique angle relative to the first tube leg, with an upper terminal end of the first central tube leg spaced from the second tube leg, with a conical mounting sleeve thereto formed of a pliable sealing material arranged for reception within the outlet conduit of the reservoir. A flexible hose is thereafter securable to a free terminal end of the second tube leg. A modification of the invention includes a second tube leg mounting a sanitizing barrel slidably mounted between a plurality of spaced flanges about the second tube leg to permit sanitizing of the second tube leg, wherein the sanitizing barrel includes a sanitizing fluid dispensing wiping web mounted between the barrel and the second tube leg.

2 Claims, 4 Drawing Sheets

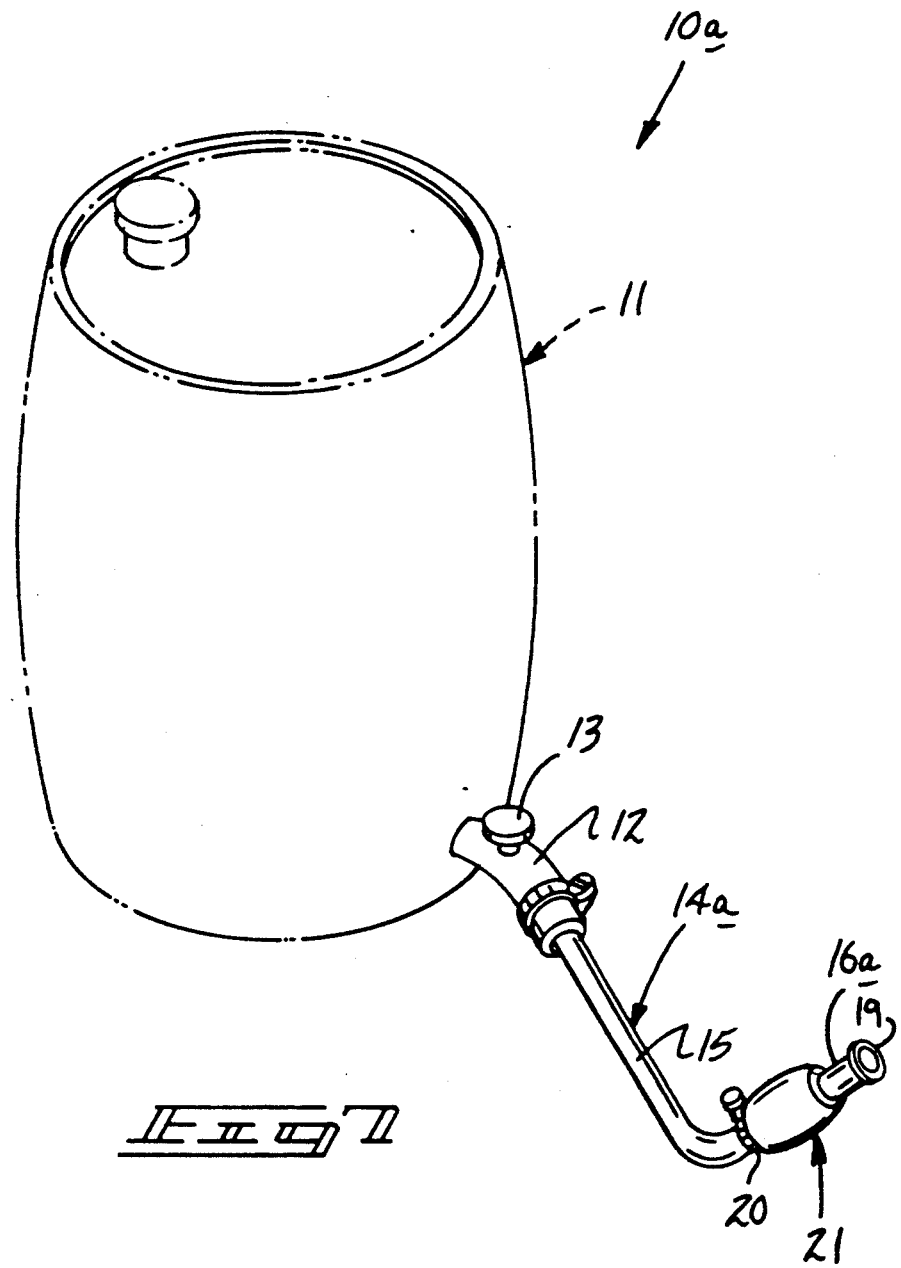

DRINKING FOUNTAIN APPARATUS

BACKGROUND OF THE INVENTION

1. Field of the Invention

The field of invention relates to drinking apparatus, and more particularly pertains to a new and improved drinking fountain apparatus wherein the same is arranged for providing convenience of dispensing of drinking fluid at remote locations.

2. Description of the Prior Art

The provision of fresh and cooling refreshment at various locations such as construction sites, picnic areas, and the like is available in the prior art. Typically, fluid dispensing devices have included outlet conduits of a relatively limited length relative to the reservoir providing access to the outlet conduits in an inconvenient and inefficient procedure in receiving fluid from the reservoir. Various portable fluid dispensing devices are utilized in the prior art and their construction is exemplified in U.S. Pat. No. 4,699,319 to Green wherein a fluid dispensing container is provided with an elongate tubular conduit of generally serpentine configuration formed as a flexible drinking straw to permit a patient to receive refreshment therefrom.

U.S. Pat. No. 4,898,290 to Cueto sets forth a baby bottle feeding device with an elongate conduit directed from the bottle to a nipple for reception by an infant.

U.S. Pat. No. 4,886,176 to Steakley sets forth a portable liquid cooler formed with an elongate flexible outlet tube.

U.S. Pat. No. 4,428,490 to Holloway sets forth a drinking vessel formed with an elongate integral straw.

As such, it may be appreciated that there continues to be a need for a new and improved drinking fountain apparatus as set forth by the instant invention which addresses both the problems of ease of use as well as effectiveness in construction and in this respect, the present invention substantially fulfills this need.

SUMMARY OF THE INVENTION

In view of the foregoing disadvantages inherent in the known types of drinking fountain constructions now present in the prior art, the present invention provides a drinking fountain apparatus wherein the same is arranged for providing a selectively securable drinking fountain adjunct to an associated reservoir. As such, the general purpose of the present invention, which will be described subsequently in greater detail, is to provide a new and improved drinking fountain apparatus which has all the advantages of the prior art drinking apparatus and none of the disadvantages.

To attain this, the present invention provides a drinking fountain including a fluid reservoir with an outlet conduit and valve mounted to the reservoir adjacent a lower terminal end thereof. The outlet conduit receives a fluid directing conduit defined by a first central tube leg and a second tube leg mounted at an oblique angle relative to the first tube leg, with an upper terminal end of the first central tube leg spaced from the second tube leg, with a conical mounting sleeve thereto formed of a pliable sealing material arranged for reception within the outlet conduit of the reservoir. A flexible hose is thereafter securable to a free terminal end of the second tube leg. A modification of the invention includes a second tube leg mounting a sanitizing barrel slidably mounted between a plurality of spaced flanges about the second tube leg to permit sanitizing of the second tube leg, wherein the sanitizing barrel includes a sanitizing fluid dispensing wiping web mounted between the barrel and the second tube leg.

My invention resides not in any one of these features per se, but rather in the particular combination of all of them herein disclosed and claimed and it is distinguished from the prior art in this particular combination of all of its structures for the functions specified.

There has thus been outlined, rather broadly, the more important features of the invention in order that the detailed description thereof that follows may be better understood, and in order that the present contribution to the art may be better appreciated. There are, of course, additional features of the invention that will be described hereinafter and which will form the subject matter of the claims appended hereto. Those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new and improved drinking fountain apparatus which has all the advantages of the prior art drinking apparatus and none of the disadvantages.

It is another object of the present invention to provide a new and improved drinking fountain apparatus which may be easily and efficiently manufactured and marketed.

It is a further object of the present invention to provide a new and improved drinking fountain apparatus which is of a durable and reliable construction.

An even further object of the present invention is to provide a new and improved drinking fountain apparatus which is susceptible of a low cost of manufacture with regard to both materials and labor, and which accordingly is then susceptible of low prices of sale to the consuming public, thereby making such drinking fountain apparatus economically available to the buying public.

Still yet another object of the present invention is to provide a new and improved drinking fountain apparatus which provides in the apparatuses and methods of the prior art some of the advantages thereof, while simultaneously overcoming some of the disadvantages normally associated therewith.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 7 is an isometric illustration of the modified drinking fountain apparatus utilized by the instant invention.

DESCRIPTION OF THE PREFERRED EMBODIMENT

Figure 1:
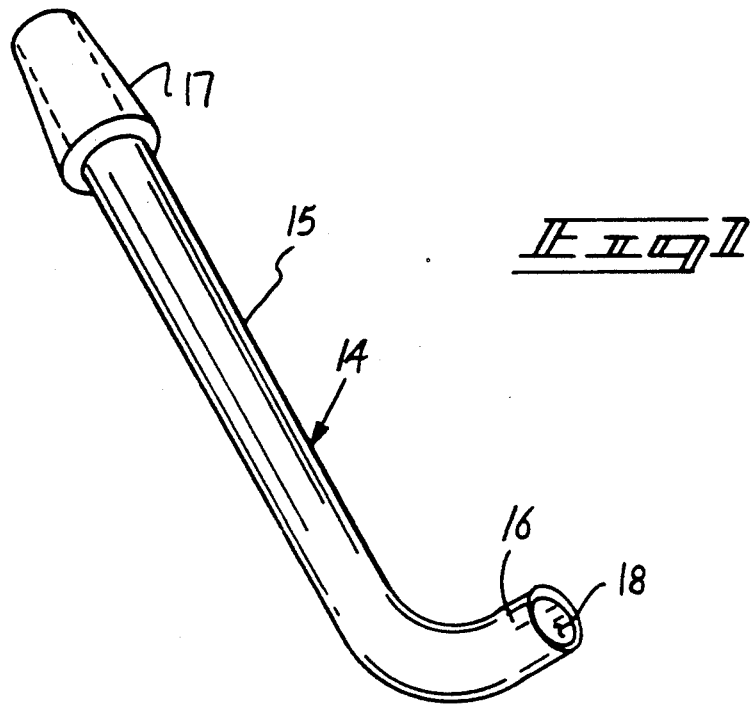
FIG. 1 is an isometric illustration of the fluid directing conduit utilized by the instant invention.
Figure 2:
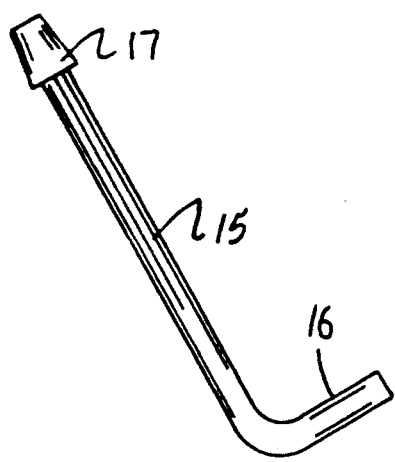
FIG. 2 is an orthographic side view of the conduit as set forth in FIG. 1.
Figure 3:
FIG. 3 is an orthographic frontal view of the conduit as set forth in FIG. 1.

With reference now to the drawings, and in particular to FIGS. 1 to 7 thereof, a new and improved drinking fountain apparatus embodying the principles and concepts of the present invention and generally designated by the reference numerals 10 and 10a will be described.

Figure 4:
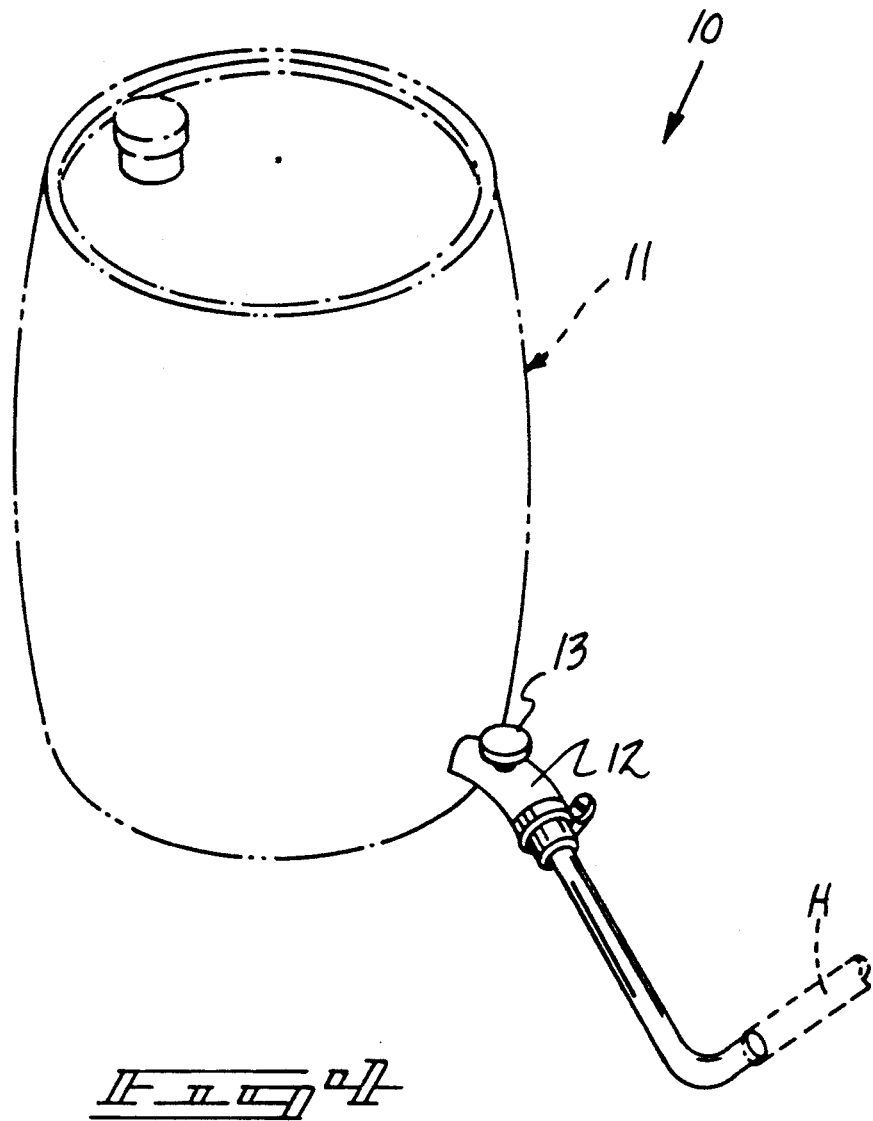
FIG. 4 is an isometric illustration of the drinking fountain apparatus in combination.
Figure 5:
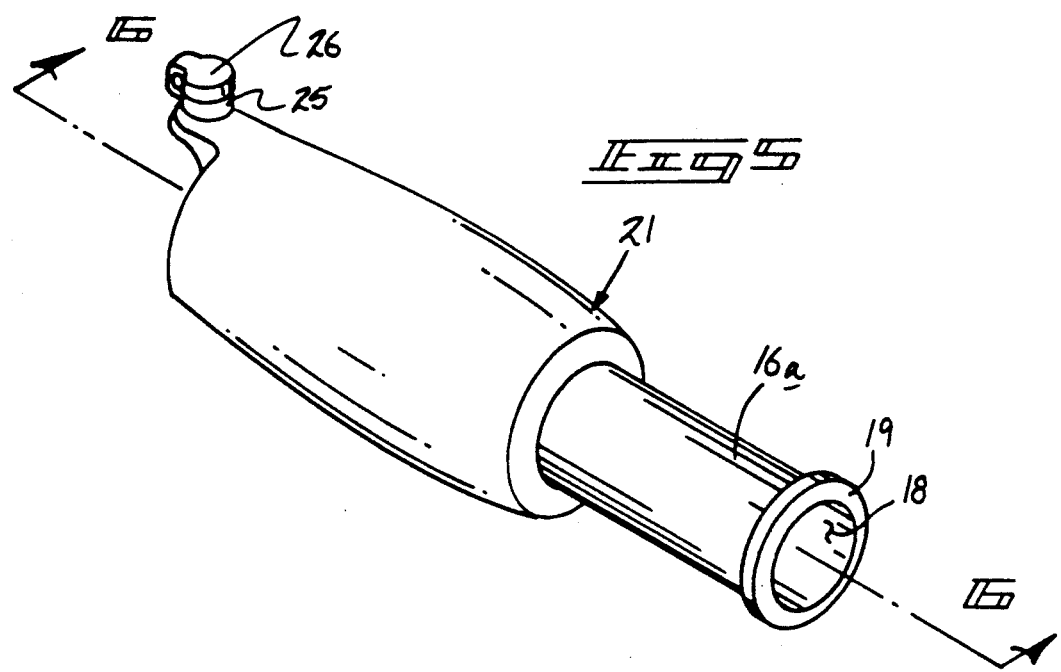
FIG. 5 is an isometric illustration of a modified fluid directing conduit second leg utilized by the instant invention.
Figure 6:
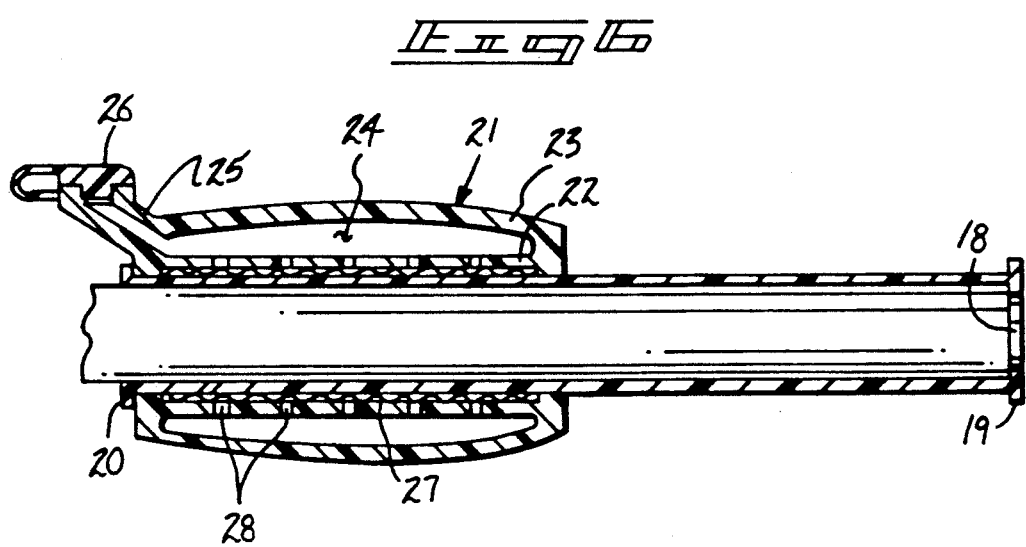
FIG. 6 is an orthographic view, taken along the lines 6—6 of FIG. 5 in the direction indicated by the arrows.

More specifically, the drinking fountain apparatus 10 of the instant invention essentially comprises a fluid reservoir 11 formed with an inlet to effect replenishment of the reservoir 11 mounted to the top surface thereof, wherein a fluid outlet conduit 12 is in fluid communication with the fluid reservoir 11 and includes a valve 13 to effect selective release of fluid from the fluid reservoir 11 through the outlet conduit 12. Rigid fluid directing conduit 14 is provided, with a first central tube leg 15 obliquely mounted to a second central tube leg 16. The fluid directing conduit 14 may be formed of a "J" shaped configuration or of an "L" shaped configuration, as illustrated, and may be formed as an example with a radius of curvature of one and one-half inches relative the intersection of the first central tube leg 15 with the second central tube leg 16. A conical mounting sleeve 17 is mounted in surrounding relationship relative to an upper terminal end of the first central tube leg 15 for reception with the fluid outlet conduit 12 and may further use a surrounding clamp about the outlet conduit 12 relative to the conical mounting sleeve 17, in a manner as illustrated in FIG. 4 for example. The conical mounting sleeve 17 is formed of a pliant sealing material to effect a sealing relationship between the first central tube leg 15 and the fluid outlet conduit 12. The second central tube leg 16 includes a second tube leg outlet opening 18 to direct fluid therethrough and for accommodation of a flexible hose "H" mounted about the outlet opening 18 if desired to provide further directional orientation of fluid from the reservoir 11. A clamp (as illustrated in FIG. 4) is mounted in surrounding relationship relative to the conical mounting sleeve 17 and the fluid outlet conduit.

A modified second central tube leg structure 16a is illustrated in FIG. 7 in coordination with a modified rigid fluid directing conduit 14a. The second central tube leg 16a includes a forward annular flange 19 positioned radially outwardly relative to the outlet opening 18 spaced from a rear annular flange 20 adjacent a junction of the first central tube leg 15 with the second central tube leg 16a. The spaced annular flanges 19 and 20 contain a sanitizing barrel 21 in a slidable relationship between the flanges 19 and 20. The sanitizing barrel 21 includes a cylindrical inner band sleeve 22 and an outer barrel wall 23 defining a fluid reservoir 24 therebetween. The fluid reservoir 24 includes a reservoir fill conduit 25 utilizing an associated conduit cap 26. The reservoir 24 is typically filled with a sanitizing fluid and directs the sanitizing fluid through the cylindrical inner barrel sleeve 22 through a matrix of inner barrel sleeve apertures 28 coextensively directed throughout the inner barrel sleeve 22. A fluid permeable cylindrical wiping web 27 is mounted contiguously between the inner barrel sleeve 22 and the exterior surface of the central second tube leg 16a, whereupon reciprocation of the barrel 21 between the flanges 19 and 20 effects sanitizing of the second tube leg 16a for subsequent use by subsequent individuals utilizing the apparatus.

As to the manner of usage and operation of the instant invention, the same should be apparent from the above disclosure, and accordingly no further discussion relative to the manner of usage and operation of the instant invention shall be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. A drinking fountain apparatus, comprising in combination, a fluid reservoir, the fluid reservoir including a fluid outlet conduit positioned through the reservoir adjacent a lower terminal end thereof, and a valve mounted within the fluid outlet conduit to effect selective fluid flow through the outlet conduit, and a rigid fluid directing conduit, the directing conduit including a first central tube leg and a second central tube leg, the second central tube leg obliquely mounted relative to the first central tube leg, with the first central tube leg including an upper terminal end spaced from the second central tube leg, with a conical mounting sleeve fixedly mounted in surrounding relationship relative to the upper terminal end of the first central tube leg, with the conical mounting sleeve formed of a pliant sealing polymeric material, and the conical mounting sleeve selectively and sealingly directed within the fluid outlet conduit, and a clamp in surrounding relationship relative to the fluid outlet conduit positioned in surrounding relationship relative to the conical mounting sleeve to enhance sealing relationship between the conical mounting sleeve and the fluid outlet conduit, and the second central tube leg includes a second tube leg outlet opening, the outlet opening spaced from the first central tube leg, and the outlet opening including a forward annular flange radially projecting about the second tube leg aligned with the outlet opening, and a rear annular flange fixedly and radially mounted and coaxially aligned relative to the forward annular flange about the second central tube leg, and a sanitizing barrel slidably mounted between the forward annular flange and the rear annular flange.

2. An apparatus as set forth in claim 1 wherein the sanitizing barrel includes an inner barrel sleeve in surrounding relationship relative to the second central tube leg and an outer barrel wall mounted to the inner barrel sleeve defining an enclosed fluid reservoir therebetween, and a reservoir fill conduit directed through the outer barrel wall into the fluid reservoir to effect selective filling of the fluid reservoir, and a fluid permeable cylindrical wiping web mounted fixedly to the inner barrel sleeve in contiguous communication with the second central tube leg, and a matrix of inner barrel sleeve apertures directed through the inner barrel sleeve in communication with the fluid reservoir, and a sanitizing fluid positioned within the fluid reservoir directed to the fluid permeable cylindrical wiping web to effect sanitizing of the second central tube leg upon reciprocating the sanitizing barrel between the forward annular flange and the rear annular flange.

* * * * *